United States Patent [19]

Musher

[11] 4,454,159

[45] Jun. 12, 1984

[54] DERMATOLOGICAL TREATMENT PREPARATIONS

[76] Inventor: Albert Musher, 17 W. 71st. St., New York, N.Y. 10023

[21] Appl. No.: 410,989

[22] Filed: Aug. 24, 1982

Related U.S. Application Data

[62] Division of Ser. No. 334,480, Dec. 28, 1981.

[51] Int. Cl.$^3$ ............................................. A61K 47/00
[52] U.S. Cl. .................................... 424/358; 424/59; 424/69; 424/236; 424/280; 424/284; 424/344; 424/359; 252/106; 252/107
[58] Field of Search ............... 424/359, 365, 284, 358, 424/199

[56] References Cited

U.S. PATENT DOCUMENTS

| | | | |
|---|---|---|---|
| 2,021,027 | 11/1935 | Snell et al. | 424/359 X |
| 2,052,028 | 8/1936 | Harris et al. | 424/359 X |
| 2,320,098 | 5/1943 | Quisling | 424/359 X |
| 2,355,029 | 8/1944 | Musher | 424/359 X |
| 2,436,818 | 3/1948 | Musher | 424/359 X |
| 2,463,738 | 3/1949 | Bernhart | 424/359 X |
| 2,876,164 | 3/1959 | Wershaw | 424/359 X |
| 4,216,201 | 8/1980 | Calro | 424/365 X |

FOREIGN PATENT DOCUMENTS

| | | | |
|---|---|---|---|
| 689937 | 7/1964 | Canada | 424/359 |
| 148545 | 12/1978 | Japan | 424/365 |
| 115812 | 9/1980 | Japan | 424/359 |
| 1439403 | 6/1976 | United Kingdom | 424/319 |
| 2092444 | 8/1982 | United Kingdom | 424/359 |

OTHER PUBLICATIONS

Jellinek Formulation & Function of Cosmetics, 5/1972, pp. 400 to 408.
Burnett, American Perfumes and Cosmetics, 10/1963, pp. 69-72, vol. 78, No. 10.

*Primary Examiner*—Dale R. Ore

[57] ABSTRACT

Preparations are provided for the treatment of irritated, pruritic and dry skin conditions by the retardation of the degenerative or chemical breakdown of the skin sebum, lipids and surface films. These objectives are accomplished by the special combination of lipids/lipoids comprising glycerol trioleate and other glyceride oils of certain fatty acid constituency and other properties, tocopherol, hydrogenated glyceride oil or fat and lecithin, more particularly in special combination with squalene or squalane, collagen protein, a humectant and isopropyl palmitate.

5 Claims, No Drawings

DERMATOLOGICAL TREATMENT PREPARATIONS

The disclosure and subject matter of my Copending Application Ser. No. 334,480 filed Dec. 28, 1981 (of which this application is a division) and of my prior applications: Ser. No. 919,061 filed June 26, 1978; Ser. No. 766,438 filed Feb. 7, 1977; Ser. No. 553,141 filed Feb. 26, 1975; Ser. No. 301,226 filed Oct. 26, 1972, Ser. No. 119,887 filed Mar. 1, 1971; and Ser. No. 791,784 filed Jan. 16, 1969 are incorporated herein by reference, and each is a continuation or a continuation-in-part of the prior field, then-copending application, all now abandoned.

The present invention relates to dermatological treatment preparations for irritated, pruritic and dry skin conditions.

The objectives of this invention are to control or retard the degenerative or chemical breakdown of the skin sebum, lipids, protein, exudates or surface films so as to provide improved skin protection, skin conditioning, and skin therapy in pruritic, keratinaceous and degenerative skin conditions. The new dermatological products pretaining to this invention will be described and set forth in the more detailed description below.

I have found that in conditions such as itching, dry, roughened, sensitive or irritated skin conditions such as sunburn, poison ivy, diaper rash, pruritus ani, and flaky or keratinaceous dry skin problems, the products of this invention aid in providing relief, skin therapy or healing as well as protection against the various conditions and stimuli that produce these skin problems.

Still further objects and advantages will appear in the more detailed description set forth below, it being understood, however, that this more detailed description is given by way of illustration and explanation only and not by way of limitation, since various changes therein may be made by those skilled in the art without departing from the scope and spirit of the present invention.

In carrying out this invention, I utilize a lipid blend comprising a special combination of lipids/lipoids which include glycerol trioleate and certain other glyceride oils (particularly triglycerides), tocopherol, a hydrogenated oil or fat (such as plastic hydrogenated shortening identified by the product sold commercially under the trade name "Crisco"), lecithin and fatty acids, as required. More particularly, I utilize the above lipid/lipoid blend in a specific combination comprising squalene or squalane, a collagen protein, a humectant and isopropyl palmitate.

The lipids used in this invention should be those rich in tocopherol and/or antioxygenic properties and/or specific fatty acids as indicated in this application. Examples of such lipids are safflower (regular or high oleic), sunflowerseed, wheat germ, corn, soya, rapeseed, palm kernel, cocoa butter, coconut, babassu, cottonseed, and peanut oils. Some of the lipid/lipoids that exhibit particular high antioxidant quality are the sunflowerseed, safflower and sesame oils and the lecithin and the plastic hydrogenated shortening.

In carrying out the objects of this invention, the lipid/lipoid blends and combinations should simulate, as closely as possible, the composition, function and/or activity of the skin lipids/lipoids. This skin simulation should include considerations of the lipid/lipoid elements such as composition and activity of the fatty acids; viscosity and plasticity qualities; adsorbency; antioxidant action; and also the drying or non-drying and saturated or unsaturated lipid characteristics.

An example of the lipid blend composition that would simulate, to the extent practicable, the desired components in the sebum or epidermal lipids would contain glyceride oils with or without added fatty acids in the approximate percentages of 20% oleic acid, 5% stearic acid, 8% myristic acid and 25% palmitic acid and linoleic acid. This lipid composition could comprise, for example, the triglyceride olive oil which contains about 70% oleic acid, the glyceride corn oil which contains about 10% palmitic and 50% linoleic acids, and the glyceride palm kernel oil which contains about 16% myristic acid.

The glycerol trioleate, with a typical fatty acid composition of approximately 5% palmitic, 2% stearic, 81% oleic and 12% linoleic, could be adjusted with safflower oil to increase the linoleic fatty acid to over approximately 20% or 30%; or the glyceride oil composition could be adjusted to contain at least 22% palmitic and oleic acids.

The hydrogenated glyceride oil or fat may be partially or more fully hydrogenated, and may be prepared from a single glyceride oil or a combination of glyceride oils and/or fats.

The lipid/lipoid component of this invention may be prepared with added fatty acids such as oleic, stearic, palmitoleic, myristoleic, lauric and myristic to adjust the fatty acid and constituency as required to simulate normal skin composition or function.

In this invention, I utilize the tocopherols in their various forms such as, for example, d-alpha tocopherol, dl-alpha tocopherol, dl-tocopherol acetate, Vitamin E oil and the mixed tocopherols, either natural or synthetic.

The further unique result of this invention is produced by special combination of the herein described lipid/lipoid blend with squalene or squalane, collagen protein, a humectant and isopropyl palmitate.

The protein component of this invention, in combination with the lipid/lipoid component, should provide adsorbency and should aid in developing improved oil-water or lipid/lipoid-water balance of the surface film of the skin. Preferable proteins are those that contain at least 1% to 15% of one or more of the following amino acids: glutamic, cystine, leucines, prolines, serine and lysine. Collagen or collagen-derived proteins such as collagen hydrolysate are advantageously included in the products of this invention.

The products described herein may be utilized in various forms such as ointments, creams, sprays lotions and soap or detergent liquids or bars. They may further be admixed, as desired, with antibiotics, antibacterials, antifungal agents or with body powders or with Vitamins A, C, or D, or with other medication.

I have found that the following combination of ingredients react colloidally and in other ways to produce a product that provides a much improved mechanism for maintaining proper oil-water balance of the skin and results in a product that exhibits unusual skin therapy in its substantially improved ability to relieve skin irritation and itching, irritated, dry, flaky or keratinaceous skin conditions.

Although this product may be made into soaps, ointments and other dermatological forms, the following (Example #1) is a representative formulation for a lotion incorporating this invention:

| | |
|---|---|
| Glycerol trioleate | 4.0% |
| Sesame Oil | 1.5% |
| Peanut Oil | 1.5% |
| Plastic hydrogenated shortening | 7.5% |
| Isopropyl palmitate | 9.0% |
| Squalane | 1.5% |
| Dl-Alpha tocopherol | 0.21% |
| Lecithin (Concentrated liquid) | 1.0% |
| Sorbitol | 1.0% |
| Collagen hydrolysate | 1.0% |
| Preservatives | 0.79% |
| Water | 61.9% |
| Stabilizers and emulsifying agents | 9.0% |
| Fragrance | 0.1% |
| | 100.0% |

Adjust with Lactic Acid to pH 6.5

An example of the lipid/lipoid combination of this invention follows:

| | |
|---|---|
| Glycerol trioleate | 14.0% |
| Sesame Oil | 6.0% |
| Peanut Oil | 5.0% |
| Wheat Germ Oil | 4.0% |
| Olive Oil | 5.0% |
| Sunflowerseed oil | 6.0% |
| Safflower Oil | 4.0% |
| Dl-Alpha Tocopherol | 1.5% |
| Lecithin | 6.5% |
| Plastic hydrogenated shortening | 48.0% |
| | 100.0% |

In place of the sesame, peanut, wheat germ, olive, sunflowerseed and safflower oils in the above lipid/lipoid combination, there may be substituted a lipid/lipoid formula such as the following—(A) olive oil 10%, safflower oil 10%, sesame oil 10%;—(B) high oleic saflower oil 8%, regular safflower oil 8%, corn oil 8%, cocoa butter 6%;—(C) safflower oil 15%, sunflowerseed oil 15%;—(D) peanut oil 8%, safflower oil 8%, sesame oil 8%, olive oil 6%.

In any of the lipid/lipoid combinations, the fatty acids (such as myristic, lauric, palmitic, stearic, linoleic) may be added, singly or in combination, to adjust to the fatty acid requirements for the final preparation.

Any of the lipid/lipoid combinations may then be utilized in following (Example #2) representative lotion formula:

| | |
|---|---|
| The above lipid/lipoid combination | 16.0% |
| Sorbitol | 1.35% |
| Collagen hydrolysate | 1.36% |
| Squalane | 1.25% |
| Isopropyl palmitate | 8.0% |
| Preservatives | 0.79% |
| Water | 62.15% |
| Stabilizers and emulsifying agents | 9.0% |
| Fragrance | 0.1% |
| | 100.0% |

Adjust with Lactic Acid to pH 6.5%.

The constituents of the lipid/lipoid blend preferably should range as follows: glycerol trioleate 11% to 30%; glyceride oil composition 15% to 45%; hydrogenated glyceride oil or fat 35% to 55%; tocopherol 0.5% to 8%; lecithin 2% to 12%. The lipid/lipoid blend may then be mixed with the other constituents in this invention so that the total claimed constituents (which do not include water, stabilizers, emulsifying agents, fragrance) are within the following ranges: the lipid/lipoid blend 40% to 78%; collagen product 2% to 12%; humectant 2% to 12%; squalene or squalane 3% to 14%; isopropyl palmitate 18% to 45%.

What I claim is:

1. A soothing, dry skin, conditioning dermatological preparation consisting of a lipid/lipoid blend which consists essentially of 11% to 30% glycerol trioleate; 15 to 45% of a glyceride oil composition comprising one or more oils selected from the following group consisting of peanut oil, sesame oil, cocoa butter, olive oil, corn oil, wheat germ oil, safflower oil, palm kernel oil and sunflower seed oil; 35% to 55% hydrogenated glyceride oil or fat; 2% to 12% lecithin; 0.5% to 8% of a tocopherol selected form the group consisting of d-alpha tocopherol, dl-tocopherol acetate, dl-tocopherol and Vitamin E oil; said lipid/lipoid blend being combined within the range of 40% to 78% with the additional constituents consisting of 2% to 12% of a humectant selected from the group consisting of sorbitol, glycerine and sugar; 18% to 45% isopropyl palmitate; 3% to 14% squalene or squalane; and a collagen product product selected from the group consisting of a protein derived from collagen, collagen hydrolysate and soluble collagen the percentage ranges of the additional constituents being based on the weight of the total claimed constituents.

2. The preparation of claim 1, the glyceride oil composition containing at least 22% palmitic and oleic acids.

3. The preparation of claim 1, the glycerol trioleate being adjusted with safflower oil to increase the linoleic fatty acid to over 20%.

4. The preparation of claim 1, the approximate percentages of the active ingredients being glycerol trioleate 4%, glyceride oil composition 3%, hydrogenated glyceride oil or fat 7.5%, lecithin 1%, squalene or squalane 1.5%, collagen product 1%, humectant 1%, tocopherol 0.21% and isopropyl palmitate 9%; the balance being water, perservatives, stabilizers, emulsifying agents and fragrance.

5. The preparation of claim 1, a representative formula for which being:

| | |
|---|---|
| Glycerol trioleate | 4.0% |
| Sesame Oil | 1.5% |
| Peanut Oil | 1.5% |
| Plastic hydrogenated shortening | 7.5% |
| Isopropyl palmitate | 9.0% |
| Squalane | 1.5% |
| Dl-alpha tocopherol | 0.21% |
| Lecithin (concentrated liquid) | 1.0% |
| Sorbitol | 1.0% |
| Collagen hydrolysate | 1.0% |
| Water, preservatives, stabilizers, emulsifying agents and fragrance | 71.79% |
| | 100.0% |

Adjust with Lactic Acid to PH 6.5

* * * * *